US007094253B2

(12) United States Patent
Dobak, III et al.

(10) Patent No.: US 7,094,253 B2
(45) Date of Patent: Aug. 22, 2006

(54) FEVER REGULATION METHOD AND APPARATUS

(75) Inventors: John D. Dobak, III, La Jolla, CA (US); Steven A. Yon, San Diego, CA (US); Michael Magers, Encinitas, CA (US)

(73) Assignee: Innercool Therapies, Inc., San Diego, CA (US)

( * ) Notice: Subject to any disclaimer, the term of this patent is extended or adjusted under 35 U.S.C. 154(b) by 52 days.

(21) Appl. No.: 10/411,001

(22) Filed: Apr. 9, 2003

(65) Prior Publication Data

US 2003/0187489 A1    Oct. 2, 2003

Related U.S. Application Data

(63) Continuation of application No. 10/005,416, filed on Nov. 7, 2001, now Pat. No. 6,585,752, and a continuation-in-part of application No. 09/586,000, filed on Jun. 2, 2000, now Pat. No. 6,383,210, and a continuation-in-part of application No. 09/566,531, filed on May 8, 2000, now abandoned, which is a continuation of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019.

(60) Provisional application No. 60/246,620, filed on Nov. 7, 2000.

(51) Int. Cl.
 *A61F 7/00* (2006.01)
(52) U.S. Cl. .................. 607/106; 607/104; 607/105
(58) Field of Classification Search ................ 607/96, 607/104–107

See application file for complete search history.

(56) References Cited

U.S. PATENT DOCUMENTS

| 1,011,606 | A | 12/1911 | Fulton |
| 2,148,541 | A | 2/1939 | Dierker |
| 2,308,484 | A | 1/1943 | Auzin et al. |
| 2,374,609 | A | 4/1945 | McCollum |
| 2,466,042 | A | 4/1949 | Reich |
| 2,615,686 | A | 10/1952 | Davidson |
| 2,672,032 | A | 3/1954 | Towse |
| 2,913,009 | A | 11/1959 | Kuthe |
| 3,125,096 | A | 3/1964 | Antiles et al. |
| 3,298,371 | A | 1/1967 | Lee |
| 3,425,419 | A | * 2/1969 | Dato .......................... 607/106 |
| 3,460,538 | A | 8/1969 | Armstrong |
| 3,504,674 | A | 4/1970 | Swenson et al. |

(Continued)

FOREIGN PATENT DOCUMENTS

AU            685559 B2      1/1998

(Continued)

OTHER PUBLICATIONS

Heder, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

(Continued)

*Primary Examiner*—Roy D. Gibson
(74) *Attorney, Agent, or Firm*—Mayer & Williams PC; Mark D. Wieczorek, Esq.; Karin L. Williams, Esq.

(57) ABSTRACT

A device and method for providing body cooling for treating fever. The cooling device applies cooling to blood flowing in a vein or artery, e.g., the vena cavae, that is then distributed throughout the body.

2 Claims, 5 Drawing Sheets

U.S. PATENT DOCUMENTS

| | | |
|---|---|---|
| 3,604,419 A | 9/1971 | Diskin et al. |
| 3,612,175 A | 10/1971 | Ford et al. |
| 3,768,484 A | 10/1973 | Gawura |
| 3,839,621 A | 10/1974 | Hariu |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,127,365 A | 11/1978 | Martin et al. |
| 4,153,048 A | 5/1979 | Magrini |
| 4,160,455 A | 7/1979 | Law |
| 4,165,206 A | 8/1979 | Martin et al. |
| 4,190,033 A | 2/1980 | Foti |
| 4,216,767 A | 8/1980 | Aoshiro |
| 4,231,425 A | 11/1980 | Engstrom |
| 4,241,729 A | 12/1980 | Aoshiro |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,375,941 A | 3/1983 | Child |
| 4,427,009 A | 1/1984 | Wells et al. |
| 4,445,500 A | 5/1984 | Osterholm |
| 4,464,172 A | 8/1984 | Lichtenstein |
| 4,483,341 A | 11/1984 | Witteles |
| 4,484,586 A | 11/1984 | McMickle et al. |
| 4,493,625 A | 1/1985 | Pieters |
| 4,497,890 A | 2/1985 | Helbert |
| 4,502,286 A | 3/1985 | Okada et al. |
| 4,569,355 A | 2/1986 | Bitterly |
| 4,581,017 A | 4/1986 | Sahota |
| 4,585,056 A | 4/1986 | Oscarsson |
| 4,602,642 A | 7/1986 | O'Hara |
| 4,638,436 A | 1/1987 | Badger et al. |
| 4,655,746 A | 4/1987 | Daniels et al. |
| 4,672,962 A | 6/1987 | Hershenson |
| 4,731,072 A | 3/1988 | Aid |
| 4,739,492 A | 4/1988 | Cochran |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,033 A | 11/1988 | Steyert et al. |
| 4,781,799 A | 11/1988 | Herbert, Jr. et al. |
| 4,789,000 A | 12/1988 | Aslanian |
| 4,796,640 A | 1/1989 | Webler |
| 4,817,624 A | 4/1989 | Newbower |
| 4,819,655 A | 4/1989 | Webler |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,917,687 A | 4/1990 | O'Boyle |
| 4,920,963 A | 5/1990 | Brader |
| 4,951,677 A | 8/1990 | Crowley et al. |
| 4,964,409 A | 10/1990 | Tremulis |
| 4,973,493 A | 11/1990 | Guire |
| 4,979,959 A | 12/1990 | Guire |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,151,578 A | 9/1992 | Phillips |
| 5,156,151 A | 10/1992 | Imran |
| 5,174,285 A | 12/1992 | Fontenot |
| 5,180,364 A | 1/1993 | Ginsburg |
| 5,180,896 A | 1/1993 | Gibby et al. |
| 5,190,539 A | 3/1993 | Fletcher et al. |
| 5,191,883 A | 3/1993 | Lennox et al. |
| 5,196,024 A | 3/1993 | Barath |
| 5,197,466 A | 3/1993 | Marchosky et al. |
| 5,211,631 A | 5/1993 | Sheaff |
| 5,226,286 A | 7/1993 | Mo |
| 5,234,405 A | 8/1993 | Klatz et al. |
| 5,234,413 A | 8/1993 | Wonder et al. |
| 5,236,908 A | 8/1993 | Gruber et al. |
| 5,239,999 A | 8/1993 | Imran |
| 5,241,951 A | 9/1993 | Mason et al. |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,279,299 A | 1/1994 | Imran |
| 5,281,213 A | 1/1994 | Milder et al. |
| 5,281,215 A | 1/1994 | Milder |
| 5,284,423 A | 2/1994 | Holdsworth et al. |
| 5,295,949 A | 3/1994 | Hathaway |
| 5,306,261 A | 4/1994 | Alliger et al. |
| 5,310,440 A | 5/1994 | Zingher |
| D347,890 S | 6/1994 | Eads |
| D348,101 S | 6/1994 | Poli et al. |
| 5,320,503 A | 6/1994 | Davis |
| 5,322,514 A | 6/1994 | Steube et al. |
| 5,322,515 A | 6/1994 | Karas et al. |
| 5,322,518 A | 6/1994 | Schneider et al. |
| 5,324,319 A | 6/1994 | Mason et al. |
| 5,326,165 A | 7/1994 | Walthall et al. |
| 5,326,166 A | 7/1994 | Walthall et al. |
| 5,326,236 A | 7/1994 | Kramer et al. |
| 5,328,461 A | 7/1994 | Utterberg |
| 5,330,435 A | 7/1994 | Vaillancourt |
| 5,330,438 A | 7/1994 | Gollobin et al. |
| 5,330,519 A | 7/1994 | Mason et al. |
| 5,331,309 A | 7/1994 | Sakai |
| 5,332,399 A | 7/1994 | Grabenkort et al. |
| 5,334,179 A | 8/1994 | Poli et al. |
| 5,334,180 A | 8/1994 | Adolf et al. |
| 5,334,182 A | 8/1994 | Simons et al. |
| 5,334,188 A | 8/1994 | Inoue et al. |
| 5,334,193 A | 8/1994 | Nardella |
| 5,334,197 A | 8/1994 | Kriesel et al. |
| 5,336,190 A | 8/1994 | Moss et al. |
| 5,339,511 A | 8/1994 | Bell |
| 5,340,290 A | 8/1994 | Clemens |
| 5,342,181 A | 8/1994 | Schock et al. |
| 5,342,182 A | 8/1994 | Montoya et al. |
| 5,342,301 A | 8/1994 | Saab |
| 5,342,346 A | 8/1994 | Honda et al. |

| | | | | | | |
|---|---|---|---|---|---|---|
| 5,342,347 A | 8/1994 | Kikuchi et al. | | 5,800,493 A | 9/1998 | Stevens et al. |
| 5,342,621 A | 8/1994 | Eury | | 5,800,516 A | 9/1998 | Fine et al. |
| 5,343,734 A | 9/1994 | Maeda et al. | | 5,807,391 A | 9/1998 | Wijkamp |
| 5,344,436 A | 9/1994 | Fontenot et al. | | 5,820,593 A | 10/1998 | Safar et al. |
| 5,344,740 A | 9/1994 | Iwasawa et al. | | 5,824,030 A | 10/1998 | Yang et al. |
| 5,346,466 A | 9/1994 | Yerlikaya et al. | | 5,827,222 A | 10/1998 | Klatz et al. |
| 5,352,213 A | 10/1994 | Woodard | | 5,827,237 A | 10/1998 | Macoviak et al. |
| 5,354,186 A | 10/1994 | Murtuza et al. | | 5,827,269 A | 10/1998 | Saadat |
| 5,354,264 A | 10/1994 | Bae et al. | | 5,833,671 A | 11/1998 | Macoviak et al. |
| 5,354,272 A | 10/1994 | Swendson et al. | | 5,833,673 A | 11/1998 | Ockuly et al. |
| 5,358,486 A | 10/1994 | Saab | | 5,834,465 A | 11/1998 | Olney |
| 5,364,364 A | 11/1994 | Kasvikis et al. | | 5,837,003 A | 11/1998 | Ginsburg |
| 5,365,750 A | 11/1994 | Greenthal | | 5,861,021 A | 1/1999 | Thome et al. |
| 5,368,591 A | 11/1994 | Lennox et al. | | 5,868,735 A | 2/1999 | Lafontaine |
| 5,383,854 A | 1/1995 | Safar et al. | | 5,871,468 A | 2/1999 | Kramer et al. |
| 5,383,918 A | 1/1995 | Panetta | | 5,871,526 A | 2/1999 | Gibbs et al. |
| 5,395,311 A | 3/1995 | Andrews | | 5,873,835 A | 2/1999 | Hastings et al. |
| 5,395,314 A | 3/1995 | Klatz et al. | | 5,879,316 A | 3/1999 | Safar et al. |
| 5,395,331 A | 3/1995 | O'Neill et al. | | 5,879,329 A | 3/1999 | Ginsburg |
| 5,403,281 A | 4/1995 | O'Neill et al. | | 5,891,094 A | 4/1999 | Masterson et al. |
| 5,405,371 A | 4/1995 | Augustine et al. | | 5,899,898 A | 5/1999 | Arless et al. |
| 5,417,686 A | 5/1995 | Peterson et al. | | 5,899,899 A | 5/1999 | Arless et al. |
| 5,423,745 A | 6/1995 | Todd et al. | | 5,902,268 A | 5/1999 | Saab |
| 5,423,807 A | 6/1995 | Milder | | 5,906,588 A | 5/1999 | Safar et al. |
| 5,433,740 A | 7/1995 | Yamaguchi | | 5,906,594 A | 5/1999 | Scarfone et al. |
| 5,437,673 A | 8/1995 | Baust et al. | | 5,906,636 A | 5/1999 | Casscells, III et al. |
| 5,443,456 A | 8/1995 | Alliger et al. | | 5,910,104 A | 6/1999 | Dobak, III et al. |
| 5,462,521 A | 10/1995 | Brucker et al. | | 5,913,856 A | 6/1999 | Chia et al. |
| 5,466,131 A | 11/1995 | Altham et al. | | 5,913,885 A | 6/1999 | Klatz et al. |
| 5,472,418 A | 12/1995 | Palestrant | | 5,913,886 A | 6/1999 | Soloman |
| 5,486,204 A | 1/1996 | Clifton | | 5,916,242 A | 6/1999 | Schwartz |
| 5,486,208 A | 1/1996 | Ginsburg | | 5,957,917 A | 9/1999 | Doiron et al. |
| 5,496,271 A | 3/1996 | Burton et al. | | 5,957,963 A | 9/1999 | Dobak, III |
| 5,496,311 A | 3/1996 | Abele et al. | | 5,964,751 A | 10/1999 | Amplatz et al. |
| 5,499,973 A | 3/1996 | Saab | | 5,967,976 A | 10/1999 | Larsen et al. |
| 5,514,094 A | 5/1996 | Anello et al. | | 5,968,009 A | 10/1999 | Simán |
| 5,520,682 A | 5/1996 | Baust et al. | | 5,971,979 A | 10/1999 | Joye et al. |
| 5,531,776 A | 7/1996 | Ward et al. | | 5,989,238 A | 11/1999 | Ginsburg |
| 5,536,247 A | 7/1996 | Thornton | | 6,007,692 A | 12/1999 | Herbert et al. |
| 5,545,133 A | 8/1996 | Burns et al. | | 6,011,995 A | 1/2000 | Guglielmi et al. |
| 5,545,708 A | 8/1996 | Onwunaka et al. | | 6,019,783 A | 2/2000 | Philips et al. |
| 5,549,559 A | 8/1996 | Eshel | | 6,022,336 A | 2/2000 | Zadno-Azizi et al. |
| 5,554,119 A | 9/1996 | Harrison et al. | | 6,024,740 A | 2/2000 | Lesh et al. |
| 5,558,644 A | 9/1996 | Boyd et al. | | 6,033,383 A | 3/2000 | Ginsburg |
| 5,569,195 A | 10/1996 | Saab | | 6,042,559 A | 3/2000 | Dobak, III |
| 5,573,532 A | 11/1996 | Chang et al. | | 6,051,019 A | 4/2000 | Dobak, III |
| 5,578,008 A | 11/1996 | Hara | | 6,063,101 A | 5/2000 | Jacobsen et al. |
| 5,584,804 A | 12/1996 | Klatz et al. | | 6,096,068 A | 8/2000 | Dobak, III et al. |
| 5,588,438 A | 12/1996 | McKown et al. | | 6,106,518 A | 8/2000 | Wittenberger et al. |
| 5,591,162 A | 1/1997 | Fletcher et al. | | 6,110,168 A | 8/2000 | Ginsburg |
| 5,620,480 A | 4/1997 | Rudie | | 6,126,684 A | 10/2000 | Gobin et al. |
| 5,622,182 A | 4/1997 | Jaffe | | 6,146,411 A | 11/2000 | Noda et al. |
| 5,624,342 A | 4/1997 | Younger | | 6,146,814 A | 11/2000 | Millet |
| 5,624,392 A | 4/1997 | Saab | | 6,149,670 A | 11/2000 | Worthen et al. |
| 5,630,837 A | 5/1997 | Crowley | | 6,149,673 A | 11/2000 | Ginsburg |
| 5,643,197 A | 7/1997 | Brucker et al. | | 6,149,676 A | 11/2000 | Ginsburg |
| 5,647,051 A | 7/1997 | Neer | | 6,149,677 A | 11/2000 | Dobak, III |
| 5,653,692 A | 8/1997 | Masterson et al. | | 6,164,283 A | 12/2000 | Lesh |
| 5,676,693 A | 10/1997 | LaFontaine | | 6,165,207 A | 12/2000 | Balding et al. |
| 5,702,234 A | 12/1997 | Pieters | | 6,182,666 B1 | 2/2001 | Dobak, III |
| 5,709,654 A | 1/1998 | Klatz et al. | | 6,190,354 B1 | 2/2001 | Sell et al. |
| 5,713,941 A | 2/1998 | Robins et al. | | 6,194,899 B1 | 2/2001 | Ishihara et al. |
| 5,716,386 A | 2/1998 | Ward et al. | | 6,206,004 B1 | 3/2001 | Schmidt et al. |
| 5,730,720 A | 3/1998 | Sites et al. | | 6,224,624 B1 | 5/2001 | Lasheras et al. |
| 5,733,318 A | 3/1998 | Augustine | | 6,231,594 B1 | 5/2001 | Dae |
| 5,733,319 A | 3/1998 | Neilson et al. | | 6,231,595 B1 | 5/2001 | Dobak, III |
| 5,735,809 A | 4/1998 | Gorsuch | | 6,235,048 B1 | 5/2001 | Dobak, III |
| 5,797,878 A | 8/1998 | Bleam | | 6,238,428 B1 | 5/2001 | Werneth et al. |
| 5,799,661 A | 9/1998 | Boyd et al. | | 6,245,095 B1 | 6/2001 | Dobak, III et al. |
| 5,800,480 A | 9/1998 | Augustine et al. | | 6,251,093 B1 | 6/2001 | Valley et al. |
| 5,800,483 A | 9/1998 | Vought | | 6,251,129 B1 | 6/2001 | Dobak, III et al. |
| 5,800,486 A | 9/1998 | Thome et al. | | 6,251,130 B1 | 6/2001 | Dobak, III et al. |
| 5,800,488 A | 9/1998 | Crockett | | 6,254,626 B1 | 7/2001 | Dobak, III et al. |

| | | | | | |
|---|---|---|---|---|---|
| 6,261,312 B1 | 7/2001 | Dobak, III et al. | 2001/0041923 A1 | 11/2001 | Dobak, III |
| 6,264,679 B1 | 7/2001 | Keller et al. | 2001/0044644 A1 | 11/2001 | Keller et al. |
| 6,277,143 B1 | 8/2001 | Klatz et al. | 2001/0047191 A1 | 11/2001 | Lasersohn et al. |
| 6,287,326 B1 | 9/2001 | Pecor | 2001/0047192 A1 | 11/2001 | Lasersohn et al. |
| 6,290,697 B1 | 9/2001 | Tu et al. | 2001/0047196 A1 | 11/2001 | Ginsburg et al. |
| 6,290,717 B1 | 9/2001 | Philips | 2001/0049545 A1 | 12/2001 | Lasersohn et al. |
| 6,295,990 B1 | 10/2001 | Lewis et al. | 2002/0002394 A1 | 1/2002 | Dobak, III |
| 6,299,599 B1 | 10/2001 | Pham et al. | 2002/0004675 A1 | 1/2002 | Lasheras |
| 6,303,156 B1 | 10/2001 | Ferrigno | 2002/0007179 A1 | 1/2002 | Dobak, III et al. |
| 6,306,161 B1 | 10/2001 | Ginsburg | 2002/0007202 A1 | 1/2002 | Dobak, III et al. |
| 6,312,374 B1 | 11/2001 | von Hoffmann | 2002/0007203 A1 | 1/2002 | Gilmartin et al. |
| 6,312,452 B1 | 11/2001 | Dobak, III et al. | 2002/0016621 A1 | 2/2002 | Werneth et al. |
| 6,315,754 B1 | 11/2001 | Daoud et al. | 2002/0022823 A1 | 2/2002 | Luo et al. |
| 6,315,995 B1 | 11/2001 | Pinsky et al. | 2002/0026227 A1 | 2/2002 | Philips |
| 6,316,403 B1 | 11/2001 | Pinsky et al. | 2002/0029016 A1 | 3/2002 | Pham et al. |
| 6,319,248 B1 | 11/2001 | Nahon | 2002/0032430 A1 | 3/2002 | Luo et al. |
| 6,325,818 B1 | 12/2001 | Werneth | 2002/0032474 A1 | 3/2002 | Dobak, III et al. |
| 6,336,911 B1 | 1/2002 | Westerbeck | 2002/0040717 A1 | 4/2002 | Dobak, III |
| 6,338,727 B1 | 1/2002 | Noda et al. | 2002/0045852 A1 | 4/2002 | Saab |
| 6,354,099 B1 | 3/2002 | Bieberich | 2002/0045892 A1 | 4/2002 | Kramer |
| 6,355,029 B1 | 3/2002 | Joye et al. | 2002/0045925 A1 | 4/2002 | Keller et al. |
| 6,364,899 B1 | 4/2002 | Dobak, III | 2002/0049409 A1 | 4/2002 | Noda et al. |
| 6,368,304 B1 | 4/2002 | Aliberto et al. | 2002/0049410 A1 | 4/2002 | Noda et al. |
| 6,379,378 B1 | 4/2002 | Werneth et al. | 2002/0049484 A1 | 4/2002 | Werneth et al. |
| 6,383,210 B1 | 5/2002 | Magers et al. | 2002/0056281 A1 | 5/2002 | Bieberich |
| 6,393,320 B1 | 5/2002 | Lasersohn et al. | 2002/0066458 A1 | 6/2002 | Aliberto et al. |
| 6,405,080 B1 | 6/2002 | Lasersohn et al. | 2002/0068901 A1 | 6/2002 | Werneth |
| 6,409,747 B1 | 6/2002 | Gobin et al. | 2002/0068964 A1 | 6/2002 | Dobak, III |
| 6,416,533 B1 | 7/2002 | Gobin et al. | 2002/0077665 A1 | 6/2002 | Kordis et al. |
| 6,419,643 B1 | 7/2002 | Shimada et al. | 2002/0077680 A1 | 6/2002 | Noda |
| 6,428,563 B1 | 8/2002 | Keller | 2002/0082671 A1 | 6/2002 | Magers et al. |
| 6,432,102 B1 | 8/2002 | Joye et al. | 2002/0091378 A1 | 7/2002 | Dobak, III et al. |
| 6,432,124 B1 | 8/2002 | Worthen et al. | 2002/0091429 A1 | 7/2002 | Dobak, III et al. |
| 6,436,130 B1 | 8/2002 | Philips et al. | 2002/0091430 A1 | 7/2002 | Dobak, III et al. |
| 6,436,131 B1 | 8/2002 | Ginsburg | 2002/0095198 A1 | 7/2002 | Whitebook et al. |
| 6,447,474 B1 | 9/2002 | Balding | 2002/0095200 A1 | 7/2002 | Dobak, III et al. |
| 6,450,987 B1 | 9/2002 | Kramer | 2002/0095201 A1 | 7/2002 | Worthen et al. |
| 6,450,990 B1 | 9/2002 | Walker et al. | 2002/0099427 A1 | 7/2002 | Dobak, III |
| 6,451,045 B1 | 9/2002 | Walker et al. | 2002/0103519 A1 | 8/2002 | Dobak, III et al. |
| 6,454,792 B1 | 9/2002 | Noda et al. | 2002/0111584 A1 | 8/2002 | Walker et al. |
| 6,454,793 B1 | 9/2002 | Evans et al. | 2002/0111616 A1 | 8/2002 | Dea et al. |
| 6,458,150 B1 | 10/2002 | Evans et al. | 2002/0111657 A1 | 8/2002 | Dae et al. |
| 6,460,544 B1 | 10/2002 | Worthen | 2002/0116039 A1 | 8/2002 | Walker et al. |
| 6,461,347 B1 | 10/2002 | von Hoffmann | 2002/0116041 A1 | 8/2002 | Daoud |
| 6,464,716 B1 | 10/2002 | Dobak, III et al. | 2002/0120314 A1 | 8/2002 | Evans et al. |
| 6,468,296 B1 | 10/2002 | Dobak, III et al. | 2002/0128698 A1 | 9/2002 | Dobak, III et al. |
| 6,471,717 B1 | 10/2002 | Dobak, III et al. | 2002/0138122 A1 | 9/2002 | Worthen et al. |
| 6,475,231 B1 | 11/2002 | Dobak, III et al. | 2000/0151943 | 10/2002 | Balding |
| 6,478,811 B1 | 11/2002 | Dobak, III et al. | 2002/0151845 A1 | 10/2002 | Werneth |
| 6,478,812 B1 | 11/2002 | Dobak, III et al. | 2002/0151942 A1 | 10/2002 | Walker et al. |
| 6,482,226 B1 | 11/2002 | Dobak, III | 2002/0151944 A1 | 10/2002 | Walker et al. |
| 2001/0001830 A1 | 5/2001 | Dobak, III et al. | 2002/0151945 A1 | 10/2002 | Gobin et al. |
| 2001/0001831 A1 | 5/2001 | Dobak, III et al. | 2002/0151946 A1 | 10/2002 | Dobak, III |
| 2001/0001832 A1 | 5/2001 | Dobak, III et al. | 2002/0156421 A1 | 10/2002 | Noda et al. |
| 2001/0002442 A1 | 5/2001 | Dobak, III | 2002/0156469 A1 | 10/2002 | Yon et al. |
| 2001/0005791 A1 | 6/2001 | Ginsburg et al. | 2002/0161331 A1 | 10/2002 | Noda et al. |
| 2001/0007951 A1 | 7/2001 | Dobak, III | 2002/0169489 A1 | 11/2002 | Dobak, III et al. |
| 2001/0008975 A1 | 7/2001 | Dobak, III et al. | 2002/0169490 A1 | 11/2002 | Noda et al. |
| 2001/0009610 A1 | 7/2001 | Augustine et al. | 2002/0173834 A1 | 11/2002 | Noda et al. |
| 2001/0010011 A1 | 7/2001 | Aliberto et al. | | | |
| 2001/0011184 A1 | 8/2001 | Dobak, III et al. | | FOREIGN PATENT DOCUMENTS | |
| 2001/0011185 A1 | 8/2001 | Dobak, III et al. | | | |
| 2001/0014802 A1 | 8/2001 | Tu | AU | 730835 B2 | 3/2001 |
| 2001/0016763 A1 | 8/2001 | Lasheras et al. | AU | 739996 B2 | 10/2001 |
| 2001/0016764 A1 | 8/2001 | Dobak, III | AU | 734506 C | 11/2001 |
| 2001/0021865 A1 | 9/2001 | Dobak, III et al. | AU | 743945 B2 | 2/2002 |
| 2001/0021866 A1 | 9/2001 | Dobak, III et al. | AU | 748985 B2 | 6/2002 |
| 2001/0027333 A1 | 10/2001 | Schwartz | CA | 2177982 A1 | 6/1995 |
| 2001/0029394 A1 | 10/2001 | Dobak, III et al. | CN | 1082382 A | 2/1994 |
| 2001/0031946 A1 | 10/2001 | Walker et al. | EP | 6555225 A1 | 5/1993 |
| 2001/0032003 A1 | 10/2001 | Pecor | EP | 0664990 A3 | 11/1997 |
| 2001/0032004 A1 | 10/2001 | Werneth | EP | 0 428 505 B2 | 3/2001 |
| 2001/0039440 A1 | 11/2001 | Lasheras et al. | EP | 1172932 A2 | 7/2001 |

| | | |
|---|---|---|
| EP | 1205167 A2 | 5/2002 |
| EP | 1029520 B1 | 8/2002 |
| FR | 2447406 A1 | 11/1981 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 97/32518 | 9/1997 |
| WO | WO 97/32818 | 9/1997 |
| WO | WO 98/26831 | 6/1998 |
| WO | WO 98/31312 | 7/1998 |
| WO | WO 98/49957 | 11/1998 |
| WO | WO 99/02096 | 1/1999 |
| WO | WO 99/04211 | 1/1999 |
| WO | WO 99/37226 | 7/1999 |
| WO | WO 99/44519 | 9/1999 |
| WO | WO 99/48449 | 9/1999 |
| WO | WO 99/56812 | 11/1999 |
| WO | WO 99/66970 | 12/1999 |
| WO | WO 99/66971 | 12/1999 |
| WO | WO 99/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/53246 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 4/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/74276 | 10/2001 |
| WO | WO 01/76655 | 10/2001 |
| WO | WO 01/78580 | 10/2001 |
| WO | WO 01/87174 | 11/2001 |
| WO | WO 01/87379 | 11/2001 |
| WO | WO 01/95840 | 12/2001 |
| WO | WO 02/07793 | 1/2002 |
| WO | WO 02/19934 | 3/2002 |
| WO | WO 02/26175 | 4/2002 |
| WO | WO 02/26176 | 4/2002 |
| WO | WO 02/26285 | 4/2002 |
| WO | WO 02/26307 | 4/2002 |
| WO | WO 02/28300 | 4/2002 |
| WO | WO 02/36180 | 5/2002 |
| WO | WO 02/38091 | 5/2002 |
| WO | WO 02/43577 | 6/2002 |
| WO | WO 02/47577 | 6/2002 |
| WO | WO 02/47742 | 6/2002 |
| WO | WO 02/055129 | 7/2002 |
| WO | WO 02/056938 | 7/2002 |
| WO | WO 02/058606 | 8/2002 |
| WO | WO 02/060514 | 8/2002 |
| WO | WO 02/065941 | 8/2002 |
| WO | WO 02/069862 | 9/2002 |
| WO | WO 02/080810 | 10/2002 |

OTHER PUBLICATIONS

Behmann, F.W; "Heat Generation Control during Artificial Hypothermia: II. Theoretical Examinations"; Pflügers Archiv, Bd. 266, S. 422-446 (1958) (German article with English translation).

Behmann, F.W., et al.; "Heat Generation Control during Artificial Hypothermia I: Experimental Examination of the Influence of Anesthetic Depth"; Pflügers Archiv, Bd. 266, S. 408-421 (1958) (German article with English translation).

Behmann, F.W., et al.; Intravascular Cooling, a Method to Achieve Controllable Hypothermia; Pflügers Archive, vol. 263, pp. 145-165 (1956) (German article with English translation).

Behmann, F.W.; "Heat Generation Control during Artificial Hypothermia, an article about the economic problem of trembling stages"; Pflügers Archive, vol. 263, pp. 166-187 (1956) (German article with English translation).

Behmann, F.W.; "Regulation of heat production in experimental hypothermia of homothermal animals"; Naunyn Schmiedebergs Arch Exp Pathol Pharmakol; 228 (1-2): 126-128 (1956). (German article with English translation).

Adair, Eleanor R., *Thermoregulation in the presence of microwave fields, Handbook of Biological Effects of Electromagnetic Fields*, chapter 10:403-433.

Alfonsi, P.,. D. I. Sessler, B. Du Manoir, J-C. Levron, J-P. Le Moing, M. Chauvin, *The Effects of Meperidine and Sufentanil on the Shivering Threshold in Postoperative Patients*, Anesthesiology, Jul. 1998, 89(1):43-48.

Ambrus; *The Biphasic Nature and Temperature Dependence of the Activation of Human Plasminogen by Urokinase*; May 1979; pp. 339-347; Research Communications in Chemical Pathology and Pharmacology, vol. 24, No. 2.

Anon, "Automatic feedback instrumentation for hospital room utilizing microsensors," *IBM Technical Disclosure Bulletin(abs.)*, 29(3): 1 page, Aug. 1986.

Benzinger, T.H.; *On Physical Heart Regulation and Sense of Temperature in Man*; Naval Medical Research Institute; Physiology; vol. 45; pp. 645-659; (Feb. 26, 1959).

Bigelo; *Hypothermia, Its Possible Role in Cardiac Surgery*; Nov. 1959; pp. 849-866; Annals of Surgery, vol. 132, No. 5.

Brengelmann, George L.; *Specialized Brain Cooling in Humans?*; The FASEB Journal; vol. 7; pp. 1148-1153 (Sep. 1993).

Buggy, D., P. Higgins, C. Moran, F. O'Donovan, and M. McCarroll, *Clonidine at Induction Reduces Shivering after General Anaesthesia*, 1997, pp. 263-367, Can. J. Anaesth., vol. 44, N. 3.

Cabanac, M., *Selective Brain Cooling and Thermoregulatory Set-Point*, 1998, pp. 3-13 , Journ. of Basic & Clinical Physiology & Pharmacology, vol. 9, N. 1.

Cabanac, M.; *Selective Brain Cooling in Humans; fancy or fact?*; The FASEB Journal; vol. 7; pp. 1143-1147 (Sep. 1993).

Capogna, G. and D. Celleno, *I. V. Clonidine for Post-Extradural Shivering in Parturients: A Preliminary Study*, 1993, Brit. Journ. of Anaesth., vol. 71.

Carrol et al. "A comparison of measurements from a temporal artery thermometer and a pulmonary artery thermistor—preliminary results," Fax correspondence dated Oct. 19, 2001.

Cheatle; *Cryostripping the Long and Short Saphenous Veins*; Jan. 1993; one page; BR. J. Surg., vol. 80.

Cheng, C., T. Matsukawa, D.I. Sessler, M. Ozaki, A. Kurz, B. Merrifield, L. Hank, and P. Olofsson, *Increasing Mean Skin Temperature Linearly Reduces the Core-Temperature Thresholds for Vasoconstriction and Shivering in Humans*, May 1995, pp. 1160-1168, Anesthesiology, vol. 82, No. 5.

Colvett, K. T., A. F. Althausen, B. Bassil, N. M. Henry, F. V. McGovern, H. H. Young, II, D. S. Kaufman, A. L. Zietman, and W.

U. Shipley, *Opportunities with Combined Modality Therapy for Selective Organ Preservation in Muscle-Invasive Bladder Cancer*, 1996, pp. 201-208, Journ. of Surgical Oncology, Vol. 63.

DeFord et al. "Design and evaluation of closed-loop feedback control of minimum temperatures in human intracranial tumours treated with interstitial hyperthermia," *Med. & Biol. Eng. & Comput.* 29:197-206, Mar. 1991.

Deklunder, G., M. Dauzat, J-L. Lecroart, J-J Hauser, and Y. Houdas, "Influence of Ventilation of the Face on Thermoregulation in Man during Hyper- and Hypothermia," *Eur. J. Appl. Physiol.*, 1991, 62:342-348.

Dexter; *Blood Warms as It Blows Retrograde from a Femoral Cannulation Site to the Carotid Artery During Cardiopulmonary Bypass*; Nov. 1994; pp. 393-397; Perfusion, vol. 9, No. 6.

Gentilello, L. M., "Advances in the Management of Hypothermia," *Horizons in Trauma Surgery*, 75(2):243-256. Apr. 1995.

Giesbrecht, G. G., M. S.. L. Goheen, C. E. Johnston, G. P. Kenny, G. K. Bristow, and J. S. Hayward, *Inhibition of Shivering Increases Core Temperature Afterdrop and Attenuates Rewarming in Hypothermic Humans*, 1997, 0161-7567:1630-1634, The American Physiological Society,.

Gillinov; *Superior Cerebral Protection with Profound Hypothermia During Circulatory Arrest*, Nov. 1992; pp. 1432-1439; Ann. Thorac. Surg., vol. 55.

Giuffre, M., J. Finnie, D. A. Lynam, and D. Smith, *Rewarming Postoperative Patients: Lights, Blankets, or Forced Warm Air*, Dec. 1991, pp. 387-393, Journ. of Post Anaesthesia Nursing, vol. 6, N. 6.

Gravenstein, *Temperature, Clinical Monitoring Practices*, pp. 208-210.

Guffin, A., D. Girard, and J. A. Kaplan, *Shivering Following Cardiac Surgery: Hemodynamic Changes and Reversal*, Feb. 1987, pp. 24-28, Journ. of Cardiothoracic Anesthesia, vol. 1, No. 1.

Haley, E. C. et al. "A Randomized Trial of Tirilazad Mesylate in Patients with Acute Stroke (RANTTAS)," *Stroke*, 27(9):1453-1458, 1996.

Higazi; *The Effect of Ultrasonic Irradiation and Temperature on Fibrinolytic Activity in Vitro*; Aug. 1992; p. 251-253; Thrombosis Research, vol. 69, No. 2.

Iaizzo, *Facial Warming Increases the Threshold for Shivering*, 1999; pp. 231-239, Journ. of Neurosurgical Anesthesiology, vol. 11, No. 4.

Imamaki; *Retrograde Cerebral Perfusion with Hypothermic Blood Provides Efficient Protection of the Brain*; Jul. 1995; pp. 325-333; Journal of Cardiac Surgery, vol. 10, No. 4, Part 1.

Jolin; *Management of a Giant Intracranial Aneurysm Using Surface-Heparinized Extracorporeal Circulation and Controlled Deep Hypothermic Low Flow Perfusion*; Aug. 1992; pp. 756-760; Acta Anaesthesiologica Scandinavia.

Jos. R.C. Jansen, Ph.D., et al. (1997) *Near continuous cardiac output by thermodilution*.Journal of Clinical Monitoring 13:233-239.

Keegan, M. T. et al. *Shivering Complicating the Treatment of Neurologically Impaired Surgical and Intensive Care Unit Patients*, Anesthesiology, 91(3):874-976, Sep. 1999.

Kimoto; *Open Heart Surgery under Direct Vision with the Aid of Brain-Cooling by Irrigation*; Jul. 1955; pp. 592-603; Surgery, vol. 39, No. 4.

Kogaku "Sensor technology to control artificial organs," *KLA*, 22(4):295-300, Aug. 1984 (in Japanese).

Kurz, Martin, et al.; "Naloxone, Meperidine, and Shivering."; *Anesthesiology*; 79(6):1193-1201; Dec. 1993.

Lennon, R. L., M. P. Hosking, M. A. Conover, and W. J. Perkins, *Evaluation of a Forced-Air System for Warming Hypothermic Postoperative Patients*, 1990, pp. 424-427, Anesth. Analg., vol. 70.

Leslie, K., D. I. Sessler, A. R. Bjorksten, M. Ozaki, T. Matsukawa, and M. Schroeder, *Propofol Causes a Dose-Dependent Decrease in the Thermoregulatory Threshold for vasoconstriction but has Little Effect on Sweating*, Aug. 1994, pp. 353-360, vol. 81, N. 2.

Maas, C. *Intermittent Antegrade Selective Cerebral Perfusion during Circulatory Arrest for Repair of Aortic Arch*. Perfusion, vol. 12, No. 2, pp. 127-132, 1997.

Marekovic, Z.; *Abstract of Renal Hypothermia in Situ by Venous Passages: Experimental Work on Dogs*; 1980; Eur Urol. 6(2); 1 page.

Matsukawa, T., A. Kurz, D. I. Sessler, A. R. Bjorksten, B. Merrifield, and C. Cheng, *Propofol Linearly Reduces the Vasoconstriction and Shivering Thresholds*, May 1995, pp. 1169-1180, Anesthesiology, vol. 82, No. 5.

Meden, P., K. Overgaard, H. Pedersen, G. Boysen, *Effect of Hypothermia and Delayed Thrombolysis in a Rat Embolic Stroke Model*, 1994, pp. 91-98, Acta Neurol. Scand. vol. 90.

Meden; *Effect of Hypothermia and Delayed Thrombolysis in a Rat Embolic Stroke Model*; Dec. 1993; pp. 91-98; Acta Neurologica Scandinavica.

Meden; *The Influence of Body Temperature on Infarct Volume and Thrombolytic Therapy in a Rat Embolic Stroke Model*; Feb. 1994; pp. 131-138; Brain Research, vol. 647.

Milleret, Rene; *La cryo-chirurgie danes les varices des mimbres inferieurs*; Angiologie; Supplement au No. 110.

Milleret; Abstract of *Cryosclerosis of the Saphenous Veins in Varicose Reflux in the Obese and Elderly*; Oct. 1981; one page; Phlebologie, vol. 34, No. 4.

Möller et al. "Temperature control and light penetration in a feedback interstitial laser thermotherapy system," *Int. J. Hyperthermia*, 12(1):49-63, 1996.

Olshausen et al. "An isothermal flowmeter with improved frequency response for measuring tissue blood flow," *Pflügers Arch.* 367:97-102, 1976.

Pais, S. O., K. D. Tobin, C. B. Austin, and L. Queral, *Percutaneous Insertion of the Greenfield Inferior Vena Cava Filter: Experience with Ninety-Six Patients*, Oct. 1988, pp. 460-464, Journ. of Vascular Surg., vol. 8, No. 4.

Parkins; *Brain Cooling in the Prevention of Brain Damage During Periods of Circulatory Occlusion in Dogs*; Apr. 1954; pp. 284-289; Annals of Surgery, vol. 140, No. 3.

Patton, J. H, T. C. Fabian, M. A. Croce, G. Minard, F. E. Pritchard, and K. A. Kudsk, *Prophylactic Greenfield Filters: Acute Complications and Long-Term Follow-Up*, Aug. 1996; pp. 231-237; Journ. of Trauma: Injury, Infection, and Critical Care, vol. 41, N. 2.

Piepgras; *Rapid Active Internal Core Cooling for Induction of Moderate Hypothermia in Head Injury by Use of an Extracorporeal Heat Exchanger*, Feb. 1998; pp. 311-318; Neurosurgery, vol. 42, No. 2.

Rijken; *Plasminogen Activation at Low Temperatures in Plasma Samples Containing Therapeutic Concentrations of Tissue-Type Plasminogen Activator or Other Thrombolytic Agents*; Oct. 1989; pp. 47-52; place of publication unknown.

Rohrer, M. J. and A. M. Natale, *Effect of Hypothermia on the Coagulation Cascade*, Oct. 1992, pp. 1402-1405, Critical Care Medicine, vol. 20, N. 10.

Schmid-Elsaesser, R. et al. (1999), *Combination Drug Therapy and Mild Hypothermia: A Promising Treatment Strategy for Reversible, Focal Cerebral Ischemia*, Stroke, 1891-1899, Jun.

Schwartz, A.E. et al.; (1996); *Isolated cerebral hypothermia by single carotid artery perfusion of extracorporeally cooled blood in baboons*; Neurosurgery 39(3):577-582.

Schwartz; *Cerebral Blood Flow during Low-flow Hypothermic Cardiopulmonary Bypass in Baboons*; Jun. 1994; pp. 959-964; Anesthesiology, vol. 81, No. 4.

Schwartz; *Selective Cerebral Hypothermia by Means of Transfemoral Internal Carotid Artery Catheterization*; May 1996; pp. 571-572; Radiology, vol. 201, No. 2.

Sessler, "Temperature-Monitoring and Thermal Management Guidelines," *Anesthesiology 1998; 89:1298-1300.*

Sessler, Daniel 1.; "Mild Perioperative Hypothermia"; The New England Journal of Medicine; 336:1730-1737; Jun. 12, 1997.

Sharkey, A., J. M. Lipton, M. T. Murphy, and A. H. Giesecke, *Inhibition of Postanesthestic Shivering with Radiant Heat*, Feb. 1987, pp. 249-252, Anesthesiology, vol. 66, N. 2.

Shiraki, K., N. Konda, and S. Sagawa, Esphageal and Tympanic Temperature Responses to Core Blood Temperature Changes during Hyperthermia, *J. Appl. Physiol.* 61(1):98-102 (1986).

Simon, M., C. A. Athanasoulis, D. Kim, F. L. Steinberg, D. H Porter, B. H. Byse, S. Kleshinski, S. Geller, D. E. Orron, and A. C.

Waltman; *Simon Nitinol Inferior Vena Cava Filter: Initial Clinical Experience*, Jul. 1989, pp. 99-103; Radiology.

Steen; *The Detrimental Effects of Prolonged Hypothermia and Rewarming in the Dog*; Aug. 1979 ; pp. 224-230; Anesthesiology, vol. 52, No. 3.

Vandam; *Hypothermia*; Sep. 1959; pp. 546-553; The New England Journal of Medicine.

Villamaria, F. J., C. E. Baisden, A. Hillis, M. H. Rajab, and P. A. Rinaldi, "Forced-Air Warming is No More Effective than Conventional Methods for Raising Postoperative Core Temperature After Cardiac Surgery," *Journ. Cardiothoracic and Vascular Anesth., 11(6):708-711*, Oct. 1997.

White; *Cerebral Hypothermia and Circulatory Arrest*; Jul. 1978; pp. 450-458; Mayo Clinic Proceedings, vol. 53.

Yenari; *Thrombolysis with Tissue Plasminogen Activator (TPA) is Temperature Dependent*; Jul. 1994; pp. 475-481; Thrombosis Research, vol. 77, No. 5.

Yoshihara; *Changes in Coagulation and Fibrinolysis Occurring in Dogs during Hypothermia*; Aug. 1984; pp. 503-512; Thrombosis Research, vol. 37, No. 4.

Zarins; *Circulation in Profound Hypothermia*; Nov. 1972; pp. 97-104; Journal of Surgical Research, vol. 14, N. 2.

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases*, 6(2): 100-104, 1996.

Albrecht, R., C. Wass, and W. Lanier, "Occurrence of potentially detrimentaionl temperature alterations in hospitalized patients at rosk for brain injury," *Mayo Clin. Proc. 73:629-635*, 1998.

Busto, R., W. Dietrich, M. Globus, and M. Ginsberg, "Postischemic moderate hypothermia inhibits CA1 hippocampal ischemic neuronal injury," *Neuroscience Letters 101:299-304*, 1989.

Busto, R., W. Dietrich, M. Globus, I. Valdes, P. Scheinberg, and M. Ginsberg, "Small differences in intraischemic brain temperature critically determine the extent of ischemic neuronal injury," *J. Cereb. Blood Flow Metabol. 7(6):729-738*, 1987.

Castillo, J., A. Davalos, and M. Noya, "Aggravation of acute ischemic stroke by hyperthermia is related to an excitotoxic mechanism," *Cerebrovasc. Dis. 9:22-27*, 1999.

Castillo, J., A. Davalos, and M. Noya, "Progression of ischaemic stroke and escitotoxic aminoacids," *The Lancet*, 349:79-83, Jan. 1997.

Castillo, J., A. Davalos, J. Marrugat, and M. Noya, "Timing for fever-related brain damage in acute ischemic stroke," *Stroke* 29:2455-2460, Dec. 1998.

Chan, L. L., B. S. Tan, G. J. L. Kaw, R. H. G. Lo, K. Y. Yeong, M. M. Htoo, and E. K. Tan, "Radiological Placement of 211 Central Venous Catheters: Outcome and Complications," *Ann. Acad. Med. Singapoer 28(4):481-487*, Jul. 1999.

Cobos, E., S. Dixon, and Y. K. Leung, "Prevention and management of central venous catheter thrombosis," *Current Opinion in Hematology 5:355-359*, 1998.

Coimbra, C. and T. Wieloch, "Moderate hypothermia mitigates neuronal damage in the rat brain when initiated several hours following transient cerebral ischemia," *Acta Neuropathol. 87:325-331*, 1994.

Dodek, A., J. A. Boone, R. O. Hooper, D. Kavanagh-Gray, I.L. Macdonal, and D. I. Peretz, "Complications of Coronary arteriography," *Can. Med. Assoc. J.*, 128:934-936, Apr. 1983.

Frank, S. M., S. N. Raja, C. F. Bulcao, and D. S. Goldstein, "Relative contribution of core and cutaneious temperatures to thermal comfort and autonomic responses in humans," *J. Appl. Physiol. 86(5):1588-1593*, 1999.

Frank, S. M., S. N. Rraja, C. Bulcao, and D. S. Goldstein, "Age-related thermoregulatory differences during core cooing in humans," *Am. J. Physiol Regulatory Integrative Comp. Physiol. 279:R349-R354*, 2000.

Georgilis, K., A. Plomaritoglou, U. Dafnt, Y. Bassiakos, and K. Vemmos, "Aetiology of fever in patiens with actue stroke," *Journal of Internal Medicine 246:203-209*, 1999.

Gerbrandy, J. , E. S. Snell and W. I. Cranson, "Oral, rectal, and esophageal temperatures in relation to central temperature control in man," Dept. of Medicine, St. Mary's Hospital Medical School, London. W.2., received Jul. 25, 1954.

Ginsberg, M., L. Sternau, M. Globus, W. Dietrich, and R. Busto, "Therpeutic modulation of brain temperature: relevance otischemic brain injury," *Cerebrovasc. Brain Metab. Rev. 4(3):189-225*, 1992.

Goldstein, D. S. and S. M. Frank, "The wisdom of th body revisited: the adrenomedullary response to mild core hyothermia in humans," *Endocrine Regulations*, 35:3-7, Jul. 25, 2001.

Hayes, B., "Temperature control in extracorporeal circulation," *Brit. Med. J. 2(615):430*, 1968.

Heintzen, M. P. and B. E. Strauer, "Periphere arterielle komplikationen nach herzkatheteruntersuchung," *Herz 23:4-20*, 1998. (In German).

Hessel, S. J., D. F. Adams, and H. L. Abrams, "Complications of angiography," *Radiology 128:273-281*, Feb. 1981.

Jessen, C., J. Mercer, and S. Puschmann, "Intravascular heat exchanger for conscious goats," *Pflüger Arch. 368:263-265*, 1977.

Kirkpatrick, W. G., R. M. Culpepper, and M. D. Sirmon, "Frequency of compliations with prolonged femoral vein catheterization for hemodialysis access," *Teltech Research Services: 1293-1298*, Mar. 20, 2000 (original published in *Nephron 73:58-63*, 1996.

Maher, J. and V. Hachinski, "Hypothermia as a potential treatment for cerebral ischemia," *Cerebrovasc. Brain Metab. Rev. 5(4):277-300*, 1993.

Meden, P., K. Overgaard, H. Pedersen, and G. Boysen, "The influence of body temperature on infarct volume and thrombolytic therapy in a rat embolic stroke model," *Brain Research 647:131-138*, Feb. 1994.

Mercer and Jessen, "Effects of total body core cooling on heat production of conscious goats," *Pflügers Arch. 373:259-267*, 1978.

Mian, N. Z., R. Bayly, D. M. Schreck, E. B. Besserman, and D. Richmond, "Incidence of deep venous thrombosis associated with femoral venous catheterization," *Acad. Emerg. Med.*, 4(12):1118-1121, Dec. 1997.

Minamisawa, H., M. Smith, and B. Siesjo, "The effect of mild hyperthermia and hypothermia on brain damage following 5, 10, and 15 minutes of forebrain ischemia," *Annals of Neurology 28(1):26-33*, Jul. 1990.

Morikawa, E., M. Ginsberg, W. Dietrich, R. Duncan, S. Kraydieh, M. Globus, and R. Busto, "The significance of brain temperature in focal cerebral ischemia: histopathological consequences of middle cerebral artery occlusion in the rat," *J. Cereb. Blood Flow Metab. 12(3):380-389*, 1992.

Nakashima, K. and M. Todd, "Effects of hypothermia on the rate of excitatory amino acid release after ischemic depolarization," *Stroke, 27(5):913-918*, May 1996.

Noto, T. J., L. W. Johnson, R. Krone, W. F. Weaver, D. A. Clark, J. R. Kramer, and G. W. Vetrovec, "Cardiac catherization 1990: A report of the registry of the Society for Cardiac angiography and Interventions," *Catherizations and Cardiovascular Diagnosis 24:75-83*, 1991.

Qureshi, A., J. Suarez, A. Bhardwaj, A. Yahia, R. Tamargo, and J. Ulatowski, "Early predictors of outcome in patients receiving hypervolemic and hypertensive therapy for symptomatic vasospasm after subarachnoid hemorrhage," *Crit. Care Med. 28(3):824-829*, 2000.

Reith, J. H. Jorgensen, P. Pedersen, H. Nakayama, H. Raaschou, L. Jeppesen, and T. Olsen, "Body temperature in acute stroke: relating to stroke severity, infarct size, mortality, and outcome," *The Lancet* 347:422-425, Feb. 1996.

Rousseaux, P. B. Scherperelel, M. Bernard, J. Graftieaux, and J. Guyot, "Fever and cerebral vasospasm in ruptured intracranial aneurysms," *Surg. Neurol. 14:459-465*. Dec. 1980.

Schwab, S., S. Schwarz, M. Spranger, E. Keller, M. Bertram, and W. Hacke, "Moderate hypothermia in the treatment of patients with severe middle cerebral artery infarction," *Stroke 29:2461-2466*, Sep. 1998.

Schwarz, S., K. Hafner, C. Med, A. Aschoff, and S. Schwab, "Incidence and prognostic significance of fever following intracerebral hemorrhage," *Neurology 54:354-361*, 2000.

Sindou, M., Ph. Debourdeau, and H. Benhamouda,"Facteurs pronostiques dans les anévrysmes intra-crâniens rompus," *La presse Medicale, 19(9):411-415*, Mar. 1990. (In French).

The National Institute of Neurological Disorders and Stroke rt-PA Stroke study Group, "Tissue plasminogen activator for acute ischemic stroke, " *N. Engl.J. Med. 333(24):1581-1587*, 1995.

The publications committee for the trail of ORG 10172 in acute stroke Treatment (TOAST) Investigators, *JAMA 279(16):1265-1272*, Apr. 1998.

Today's News, "Radiant medical announces data from therapeutic cooling trial for heart attack presented at American Heart Association meeting," Source: http://www.radiantmedical.com, located on Nov. 26, 2001.

Xue, D., Z-G. Huang, K. E. Smith, and A. M. Buchan, "Immediate or delayed mild hypothermia prevents focal cerebral infarction," *Brain Research 587:66-72*, 1992.

\* cited by examiner

FEVER REGULATION METHOD AND APPARATUS

CROSS REFERENCE TO RELATED APPLICATIONS

This is a continuation patent application of co-pending U.S. patent application Ser. No. 10/005,416 filed on Nov. 7, 2001, now U.S. Pat. No. 6,585,752, entitled "Fever Regulation Method and Apparatus", which is a continuation-in-part of U.S. patent application Ser. Nos: 60/246,620, filed Nov. 7, 2000, entitled "Fever Regulation Method And Apparatus"; 09/586,000, filed Jun. 2, 2000, entitled "Method For Determining The Effective Thermal Mass Of A Body Or Organ Using A Cooling Catheter", now U.S. Pat. No. 6,383,210; and 09/566,531, filed May 8, 2000, now abandoned entitled "Method Of Making Selective Organ Cooling Catheter", which is a continuation of U.S. patent application Ser. No. 09/103,342, filed on Jun. 23, 1998, entitled "Selective Organ Cooling Catheter And Method Of Using The Same", now U.S. Pat. No. 6,096,068, which is a continuation-in-part of U.S. patent application Ser. No. 09/047,012, filed Mar. 24, 1998, entitled "Selective Organ Hypothermia Method And Apparatus", now U.S. Pat. No. 5,957,963, which is a continuation-in-part of U.S. patent application Ser. No. 09/012,287, filed Jan. 23, 1998, entitled "Selective Organ Hypothermia Method And Apparatus", now U.S. Pat. No. 6,051,019, all of which are incorporated by reference herein.

STATEMENT REGARDING FEDERALLY SPONSORED RESEARCH OR DEVELOPMENT

Not Applicable

BACKGROUND OF THE INVENTION

1. Field of the Invention

The present invention relates generally to the lowering and control of the temperature of the human body. More particularly, the invention relates to a method and intravascular apparatus for cooling the whole body, especially during periods of fever.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. The currently-employed techniques and devices used to cause total body hypothermia lead to various side effects. In addition to the undesirable side effects, present methods of administering total body hypothermia are cumbersome.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a rigid metallic catheter. The catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. Thus, the Dato device cools along the length of a very elongated device. Use of the Dato device is highly cumbersome due to its size and lack of flexibility.

U.S. Pat. No. 5,837,003 to Ginsburg also discloses a method and apparatus for controlling a patient's body temperature. In this technique, a flexible catheter is inserted into the femoral artery or vein or the jugular vein. The catheter may be in the form of a balloon to allow an enhanced surface area for heat transfer. A thermally conductive metal foil may be used as part of a heat-absorbing surface. This device fails to disclose or teach use of any ability to enhance heat transfer. In addition, the disclosed device fails to disclose temperature regulation.

An ailment particular susceptible to treatment by cooling, either selective or whole body, is fever or hyperthermia. There is a growing awareness of the dangers associated with fever. Many patients, especially after surgery and/or in the intensive care unit, suffer from fever. For example, it is estimated that 90% of patients in neurointensive care units suffering from sub-arachnoid hemorrhage have a fever. Further, 60% of patients in neurointensive care units suffering from intra-cranial hemorrhage have a fever. 80% of patients in neurointensive care units suffering from traumatic brain injury have a fever. These patients are typically treated with Tylenol, cooling blankets, or other such methods. These methods are not believed to be very effective; moreover, they are difficult to control.

Therefore, a practical method and apparatus that lowers and controls the temperature of the human body satisfies a long-felt need.

SUMMARY OF THE INVENTION

In one aspect, the apparatus of the present invention can include a heat transfer element that can be used to apply cooling to the blood flowing in a large vein feeding the heart.

The heat transfer element, by way of example only, includes first and second elongated, articulated segments, each segment having a mixing-inducing exterior surface. A flexible joint can connect the first and second elongated segments. An inner lumen may be disposed within the first and second elongated segments and is capable of transporting a pressurized working fluid to a distal end of the first elongated segment. In addition, the first and second elongated segments may have a mixing-inducing interior surface for inducing mixing within the pressurized working fluid. The mixing-inducing exterior surface may be adapted to induce mixing within a blood flow when placed within an artery or vein. In one embodiment, the flexible joint includes a bellows section that also allows for axial compression of the heat transfer element as well as for enhanced flexibility.

In alternative embodiments, the bellows section may be replaced with flexible tubing such as small cylindrical polymer connecting tubes.

In one embodiment, the mixing-inducing exterior surfaces of the heat transfer element include one or more helical grooves and ridges. Adjacent segments of the heat transfer element can be oppositely spiraled to increase mixing. For instance, the first elongated heat transfer segment may include one or more helical ridges having a counter-clockwise twist, while the second elongated heat transfer segment includes one or more helical ridges having a clockwise twist. Alternatively, of course, the first elongated heat transfer segment may include one or more clockwise helical ridges, and the second elongated heat transfer segment may include one or more counter-clockwise helical ridges. The first and second elongated, articulated segments may be formed from highly conductive materials such as metals, thin polymers, or doped polymers.

The heat transfer device may also have a supply catheter with an inner catheter lumen coupled to the inner lumen within the first and second elongated heat transfer segments. A working fluid supply configured to dispense the pressurized working fluid may be coupled to the inner catheter lumen or alternatively to the supply catheter. The working fluid supply may be configured to produce the pressurized working fluid at a temperature of about 0° C. and at a pressure below about 5 atmospheres of pressure.

In yet another alternative embodiment, the heat transfer device may have three or more elongated, articulated, heat transfer segments each having a mixing-inducing exterior surface, with additional flexible joints connecting the additional elongated heat transfer segments. In one such embodiment, by way of example only, the first and third elongated heat transfer segments may include clockwise helical ridges, and the second elongated heat transfer segment may include one or more counter-clockwise helical ridges. Alternatively, of course, the first and third elongated heat transfer segments may include counter-clockwise helical ridges, and the second elongated heat transfer segment may include one or more clockwise helical ridges.

The mixing-inducing exterior surface of the heat transfer element may optionally include a surface coating or treatment to inhibit clot formation. A surface coating may also be used to provide a degree of lubricity to the heat transfer element and its associated catheter.

The present invention is also directed to a method of treating fever in the body by inserting a flexible cooling element into a vein that is in pressure communication with the heart, e.g., the femoral or iliac veins, the superior or inferior vena cavae or both. The vena cavae may be accessed via known techniques from the jugular vein or from the subclavian or femoral veins, for example. The heat transfer element in one or both vena cavae may then cool virtually all the blood being returned to the heart. The cooled blood enters the right atrium at which point the same is pumped through the right ventricle and into the pulmonary artery to the lungs where the same is oxygenated. Due to the heat capacity of the lungs, the blood does not appreciably warm during oxygenation. The cooled blood is returned to the heart and pumped to the entire body via the aorta. Thus, cooled blood may be delivered indirectly to a chosen organ such as the brain. This indirect cooling is especially effective as high blood flow organs such as the heart and brain are preferentially supplied blood by the vasculature.

A warming blanket or other warming device may be applied to portions of the body to provide comfort to the patient and to inhibit thermoregulatory responses such as vasoconstriction. Thermoregulatory drugs may also be so provided for this reason.

The method further includes circulating a working fluid through the flexible, conductive cooling element in order to lower the temperature of the blood in the vena cava. The flexible, conductive heat transfer element preferably absorbs more than about 100 or 300 Watts of heat.

The method may also include inducing mixing within the free stream blood flow within the vena cava. It is noted that a degree of turbulence or mixing is generally present within the vena cava anyway. The step of circulating may include inducing mixing in the flow of the working fluid through the flexible heat transfer element. The pressure of the working fluid may be maintained below about 5 atmospheres of pressure.

The present invention also envisions a method for lowering a fever in the body of a patient which includes introducing a catheter, with a cooling element, into a vena cava supplying the heart, the catheter having a diameter of about 18 mm or less, inducing mixing in blood flowing over the cooling element, and lowering the temperature of the cooling element to remove heat from the blood to cool the blood. In one embodiment, the cooling step removes at least about 50 Watts of heat from the blood. The mixing induced may result in a Nusselt number enhancement of the flow of between about 5 and 80.

Advantages of the invention are numerous. Patients can be provided with an efficient method of reducing fever that does not suffer from the deleterious consequences of the prior art. The procedure can be administered safely and easily. Numerous cardiac and neural settings can benefit by the hypothermic therapy. Other advantages will be understood from the following.

The novel features of this invention, as well as the invention itself, will be best understood from the attached drawings, taken along with the following description, in which similar reference characters refer to similar parts, and in which:

DETAILED DESCRIPTION OF THE INVENTION

Overview

A one or two-step process and a one or two-piece device may be employed to intravascularly lower the temperature of a body in order to treat fever. A cooling element may be placed in a high-flow vein such as the vena cavae to absorb heat from the blood flowing into the heart. This transfer of heat causes a cooling of the blood flowing through the heart and thus throughout the vasculature. Such a method and device may therapeutically be used to treat fever.

A heat transfer element that systemically cools blood should be capable of providing the necessary heat transfer rate to produce the desired cooling effect throughout the vasculature. This may be up to or greater than 300 watts, and is at least partially dependent on the mass of the patient and the rate of blood flow. Surface features may be employed on the heat transfer element to enhance the heat transfer rate. The surface features and other components of the heat transfer element are described in more detail below.

One problem with treating fever with cooling is that the cause of the patient's fever attempts to defeat the cooling. Thus, a high power device is often required.

Anatomical Placement

The internal jugular vein is the vein that directly drains the brain. The external jugular joins the internal jugular at the base of the neck. The internal jugular veins join the subclavian veins to form the brachiocephalic veins that in turn drain into the superior vena cava. The superior vena cava drains into the right atrium of the heart and supplies blood to the heart from the upper part of the body.

A cooling element may be placed into the superior vena cava, inferior vena cava, or otherwise into a vein which feeds into the superior vena cava or otherwise into the heart to cool the body. A physician may percutaneously place the catheter into the subclavian or internal or external jugular veins to access the superior vena cava. The blood, cooled by the heat transfer element, may be processed by the heart and provided to the body in oxygenated form to be used as a conductive medium to cool the body. The lungs have a fairly low heat capacity, and thus the lungs do not cause appreciable rewarming of the flowing blood.

The vasculature by its very nature provides preferential blood flow to the high blood flow organs such as the brain and the heart. Thus, these organs are preferentially cooled by such a procedure. The core body temperature may be measured by an esophageal probe. The brain temperature usually decreases more rapidly than the core body temperature. The inventors believe this effect to be due to the preferential supply of blood provided to the brain and heart. This effect may be even more pronounced if thermoregulatory effects, such as vasoconstriction, occur that tend to focus blood supply to the core vascular system and away from the peripheral vascular system.

Heat Transfer

When a heat transfer element is inserted approximately coaxially into an artery or vein, the primary mechanism of heat transfer between the surface of the heat transfer element and the blood is forced convection. Convection relies upon the movement of fluid to transfer heat. Forced convection results when an external force causes motion within the fluid. In the case of arterial or venous flow, the beating heart causes the motion of the blood around the heat transfer element.

The magnitude of the heat transfer rate is proportional to the surface area of the heat transfer element, the temperature differential, and the heat transfer coefficient of the heat transfer element.

The receiving artery or vein into which the heat transfer element is placed has a limited diameter and length. Thus, the surface area of the heat transfer element must be limited to avoid significant obstruction of the artery or vein and to allow the heat transfer element to easily pass through the vascular system. For placement within the superior vena cava via the external jugular, the cross sectional diameter of the heat transfer element may be limited to about 5–6 mm, and its length may be limited to approximately 10–15 cm. For placement within the inferior vena cava, the cross sectional diameter of the heat transfer element may be limited to about 6–7 mm, and its length may be limited to approximately 25–35 cm.

Decreasing the surface temperature of the heat transfer element can increase the temperature differential. However, the minimum allowable surface temperature is limited by the characteristics of blood. Blood freezes at approximately 0° C. When the blood approaches freezing, ice emboli may form in the blood, which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery, thus compromising the flow of blood to the brain. Given the above constraints, it is advantageous to limit the minimum allowable surface temperature of the cooling element to approximately 5° C. This results in a maximum temperature differential between the blood stream and the cooling element of approximately 32° C. For other physiological reasons, there are limits on the maximum allowable surface temperature of the warming element.

However, in certain situations, temperatures lower than 0° C. may be used. For example, certain patients may have blood flows such that the flow per se prohibits or significantly inhibits freezing. To achieve such cooling, sub-zero temperatures may be used. In these cases, working fluids such as perfluorocarbons may be employed.

The mechanisms by which the value of the convection heat transfer coefficient may be increased are complex. However, it is well known that the convection heat transfer coefficient increases with the level of "mixing" or "turbulent" kinetic energy in the fluid flow. Thus it is advantageous to have blood flow with a high degree of mixing in contact with the heat transfer element.

The blood flow has a considerably more stable flux in the vena cava than in an artery. However, the blood flow in the vena cava still has a high degree of inherent mixing or turbulence. Reynolds numbers in the superior vena cava may range, for example, from 2,000 to 5,000. Thus, blood cooling in the vena cava may benefit from enhancing the level of mixing with the heat transfer element but this benefit may be substantially less than that caused by the inherent mixing.

Boundary Layers

A thin boundary layer has been shown to form during the cardiac cycle. Boundary layers develop adjacent to the heat transfer element as well as next to the walls of the artery or vein. Each of these boundary layers has approximately the same thickness as the boundary layer that would have developed at the wall of the artery in the absence of the heat transfer element. The free stream flow region is developed in an annular ring around the heat transfer element. The heat transfer element used in such a vessel should reduce the formation of such viscous boundary layers.

Heat Transfer Element Characteristics and Description

The intravascular heat transfer element should be flexible in order to be placed within the vena cavae or other veins or arteries. The flexibility of the heat transfer element is an important characteristic because the same is typically inserted into a vein such as the external jugular and accesses the vena cava by initially passing though a series of one or more branches. Further, the heat transfer element is ideally constructed from a highly thermally conductive material such as metal in order to facilitate heat transfer. The use of a highly thermally conductive material increases the heat transfer rate for a given temperature differential between the working fluid within the heat transfer element and the blood. This facilitates the use of a higher temperature coolant, or lower temperature warming fluid, within the heat transfer element, allowing safer working fluids, such as water or saline, to be used. Highly thermally conductive materials, such as metals, tend to be rigid. Therefore, the design of the heat transfer element should facilitate flexibility in an inherently inflexible material.

However, balloon designs may also be employed, such as those disclosed in co-pending U.S. patent application Ser. No. 09/215,038, filed Dec. 16, 1998, entitled "Inflatable Catheter for Selective Organ Heating and Cooling and Method of Using the Same,", now U.S. Pat. No. 6,261,312 and incorporated herein by reference in its entirety.

It is estimated that the cooling element should absorb at least about 50 Watts of heat when placed in the vena cava to lower the temperature of the body to between about 30° C. and 34° C. These temperatures are thought to be appropriate to lower most fevers. The power removed determines how quickly the target temperature can be reached. For example, in a fever therapy in which it is desired to lower brain temperature, the same may be lowered about 4° C. per hour in a 70 kg human upon removal of 300 Watts.

One embodiment of the invention uses a modular design. This design creates helical blood flow and produces a level of mixing in the blood flow by periodically forcing abrupt changes in the direction of the helical blood flow. The abrupt changes in flow direction are achieved through the use of a series of two or more heat transfer segments, each included of one or more helical ridges. The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry. These surface features also tend to increase the surface area of the heat transfer element, further enhancing heat transfer.

Figure 1:
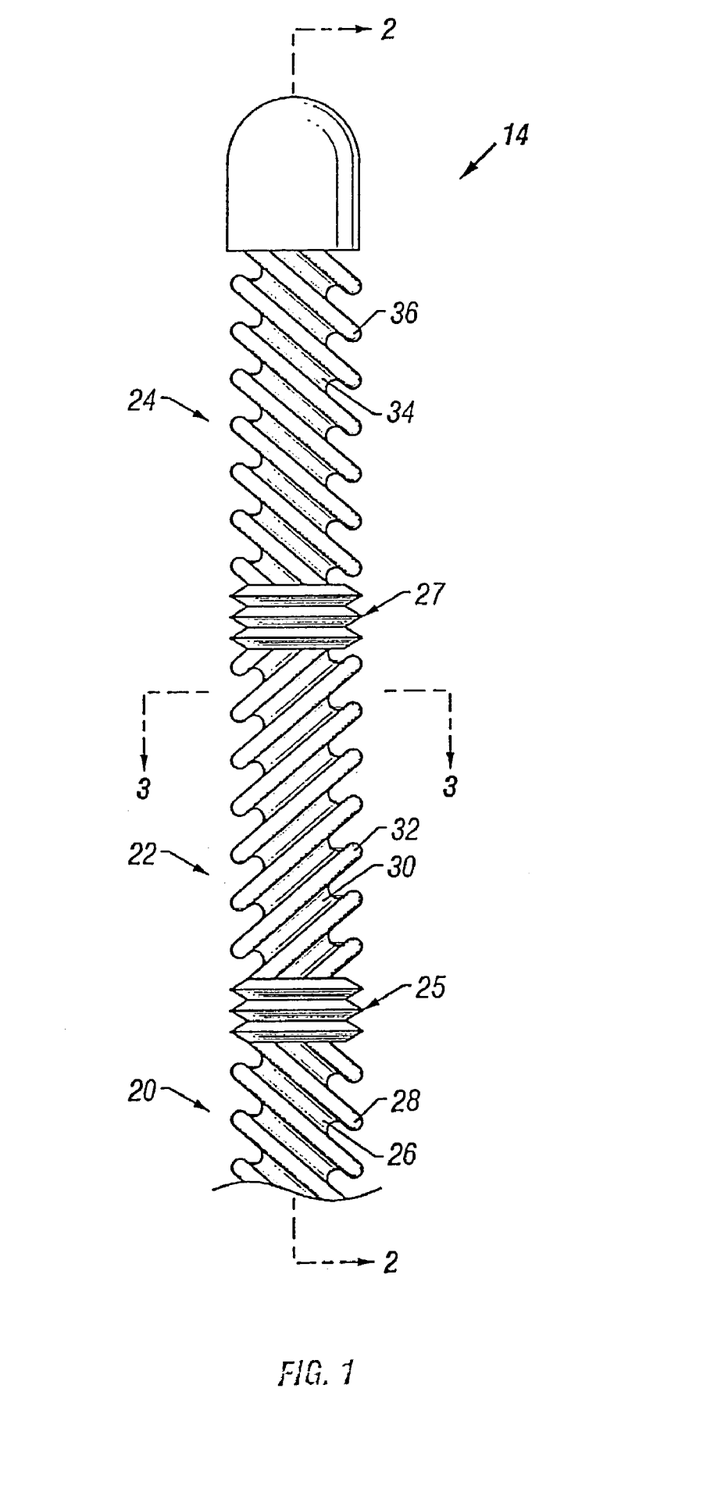
FIG. 1 is an elevation view of one embodiment of a heat transfer element according to the invention.

FIG. 1 is an elevation view of one embodiment of a cooling element 14 according to the present invention. The heat transfer element 14 includes a series of elongated, articulated segments or modules 20, 22, 24. Three such segments are shown in this embodiment, but two or more such segments could be used without departing from the spirit of the invention. As seen in FIG. 1, a first elongated heat transfer segment 20 is located at the proximal end of the heat transfer element 14. A mixing-inducing exterior surface of the segment 20 includes four parallel helical ridges 28 with four parallel helical grooves 26 therebetween. One, two, three, or more parallel helical ridges 28 could also be used without departing from the spirit of the present invention. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 25, which provides flexibility and compressibility. The second heat transfer segment 22 includes one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 27. The third heat transfer segment 24 includes one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 allow the heat transfer element 14 to maintain a relatively atraumatic profile, thereby minimizing the possibility of damage to the blood vessel wall. A heat transfer element according to the present invention may include two, three, or more heat transfer segments.

The bellows sections 25, 27 are formed from seamless and nonporous materials, such as metal, and therefore are impermeable to gas, which can be particularly important, depending on the type of working fluid that is cycled through the heat transfer element 14. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance. In alternative embodiments, the bellows may be replaced by flexible polymer tubes, which are bonded between adjacent heat transfer segments.

The exterior surfaces of the heat transfer element 14 can be made from metal, and may include very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24–48 hours or even longer, it may be desirable to treat the surfaces of the heat transfer element 14 to avoid clot formation. In particular, one may wish to treat the bellows sections 25, 27 because stagnation of the blood flow may occur in the convolutions, thus allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and thus prevent adherence of clotting factors. Another coating that provides beneficial properties may be a lubricious coating. Lubricious coatings, on both the heat transfer element and its associated catheter, allow for easier placement in the, e.g., vena cava.

Figure 2:
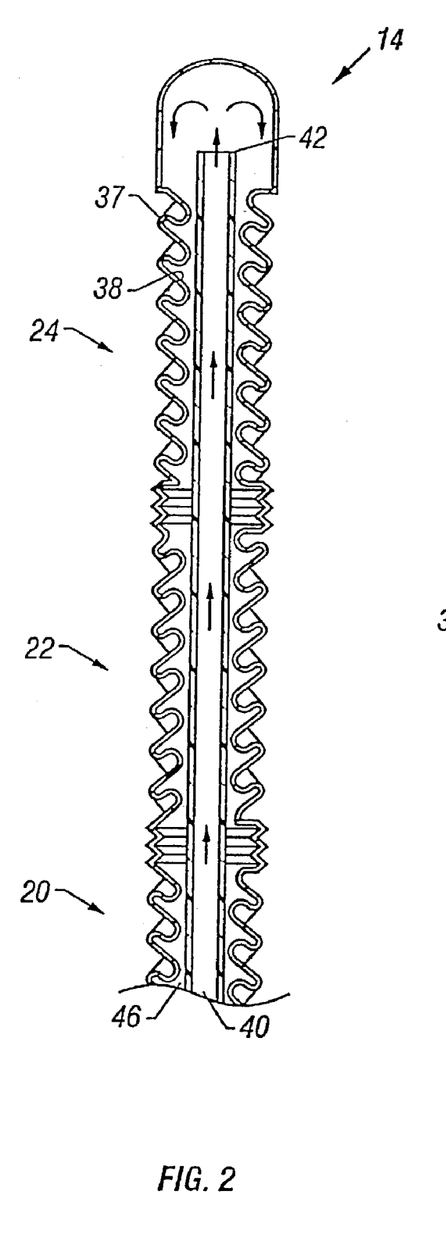
FIG. 2 is a longitudinal section view of the heat transfer element of FIG. 1.

FIG. 2 is a longitudinal sectional view of the heat transfer element 14 of an embodiment of the invention, taken along line 2—2 in FIG. 1. Some interior contours are omitted for purposes of clarity. An inner tube 42 creates an inner lumen 40 and an outer lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner lumen 40. At the distal end of the heat transfer element 14, the working fluid exits the inner lumen 40 and enters the outer lumen 46. As the working fluid flows through the outer lumen 46, heat is transferred from the working fluid to the exterior surface 37 of the heat transfer element 14. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or another polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid that remains a liquid as the working fluid. Other coolants such as Freon undergo nucleate boiling and create mixing through a different mechanism. Saline is a safe working fluid, because it is non-toxic, and leakage of saline does not result in a gas embolism, which could occur with the use of boiling refrigerants. Since mixing in the working fluid is enhanced by the shape of the interior surface 38 of the heat transfer element 14, the working fluid can be delivered to the cooling element 14 at a warmer temperature and still achieve the necessary cooling rate. Similarly, since mixing in the working fluid is enhanced by the shape of the interior surface of the heat transfer element, the working fluid can be delivered to the warming element 14 at a cooler temperature and still achieve the necessary warming rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

Figure 3:
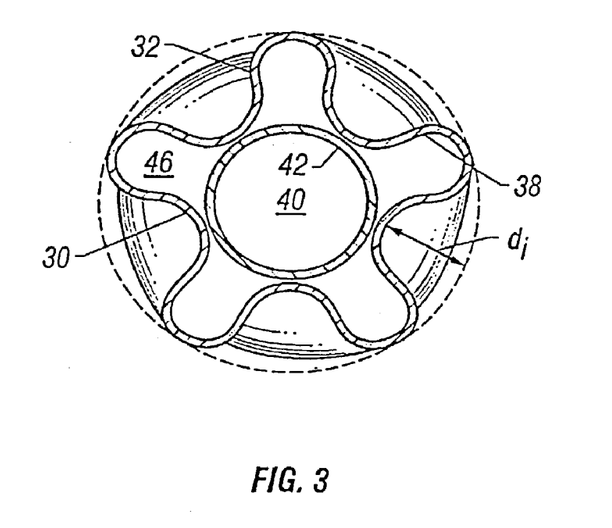
FIG. 3 is a transverse section view of the heat transfer element of FIG. 1.

FIG. 3 is a transverse sectional view of the heat transfer element 14 of the invention, taken at a location denoted by the line 3—3 in FIG. 1. FIG. 3 illustrates a five-lobed embodiment, whereas FIG. 1 illustrates a four-lobed embodiment. As mentioned earlier, any number of lobes might be used. In FIG. 3, the construction of the heat transfer element 14 is clearly shown. The inner lumen 40 is defined by the insulating tube 42. The outer lumen 46 is defined by the exterior surface of the insulating tube 42 and the interior surface 38 of the heat transfer element 14. In addition, the helical ridges 32 and helical grooves 30 may be seen in FIG. 3. Although FIG. 3 shows four ridges and four grooves, the number of ridges and grooves may vary. Thus, heat transfer elements with 1, 2, 3, 4, 5, 6, 7, 8 or more ridges are specifically contemplated.

Figure 4:
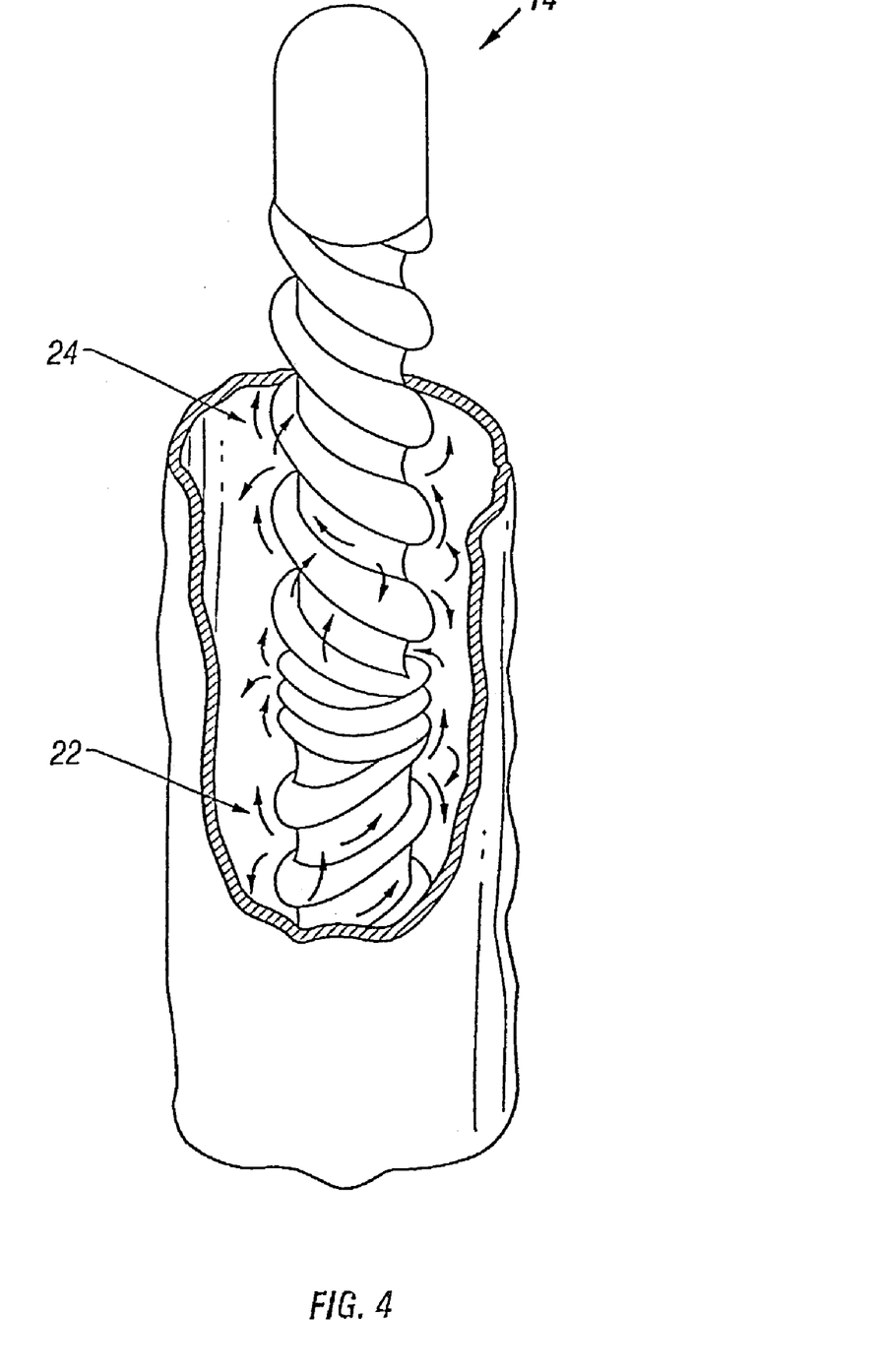
FIG. 4 is a perspective view of the heat transfer element of FIG. 1 in use within a blood vessel.

FIG. 4 is a perspective view of a heat transfer element 14 in use within a blood vessel, showing only one helical lobe per segment for purposes of clarity. Beginning from the proximal end of the heat transfer element (not shown in FIG. 4), as the blood moves forward, the first helical heat transfer segment 20 induces a counter-clockwise rotational inertia to the blood. As the blood reaches the second segment 22, the rotational direction of the inertia is reversed, causing mixing within the blood. Further, as the blood reaches the third segment 24, the rotational direction of the inertia is again reversed. The sudden changes in flow direction actively reorient and randomize the velocity vectors, thus ensuring mixing throughout the bloodstream. During such mixing, the velocity vectors of the blood become more random and, in some cases, become perpendicular to the axis of the vessel. Thus, a large portion of the volume of warm blood in the vessel is actively brought in contact with the heat transfer element 14, where it can be cooled by direct contact rather than being cooled largely by conduction through adjacent laminar layers of blood.

Referring back to FIG. 1, the heat transfer element 14 has been designed to address all of the design criteria discussed above. First, the heat transfer element 14 is flexible and is made of a highly conductive material. The flexibility is provided by a segmental distribution of bellows sections 25, 27 that provide an articulating mechanism. Bellows have a known convoluted design that provide flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote mixing both internally and externally. The modular or segmental design allows the direction of the grooves to be reversed between segments. The alternating helical rotations create an alternating flow that results in mixing the blood in a manner analogous to the mixing action created by the rotor of a washing machine that switches directions back and forth. This action is intended to promote mixing to enhance the heat transfer rate. The alternating helical design also causes beneficial mixing, or turbulent kinetic energy, of the working fluid flowing internally.

Method of Use

The practice of the present invention is illustrated in the following non-limiting example.

EXEMPLARY PROCEDURE

1. The patient is initially assessed as having a fever, resuscitated, and stabilized.
2. The procedure may be carried out in an angiography suite, NICU, ICU, or surgical suite equipped with fluoroscopy.
3. An ultrasound or angiogram of the superior vena cava and external jugular can be used to determine the vessel diameter and the blood flow; a catheter with an appropriately sized heat transfer element can be selected.

4. After assessment of the veins, the patient is sterilely prepped and infiltrated with lidocaine at a region where the appropriate vein may be accessed.
5. The external jugular is cannulated and a guide wire may be inserted to the superior vena cava. Placement of the guide wire is confirmed with fluoroscopy.
6. An angiographic catheter can be fed over the wire and contrast media injected into the vein to further to assess the anatomy if desired.
7. Alternatively, the external jugular is cannulated and a 10–12.5 french (f) introducer sheath is placed.
8. A guide catheter is placed into the superior vena cava. If a guide catheter is placed, it can be used to deliver contrast media directly to further assess anatomy.
9. The cooling catheter is placed into the superior vena cava via the guiding catheter or over the guidewire.
10. Placement is confirmed if desired with fluoroscopy.
11. Alternatively, the cooling catheter shaft has sufficient pushability and torqueability to be placed in the superior vena cava without the aid of a guide wire or guide catheter.
12. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
13. Cooling is initiated by starting the pump mechanism. The saline within the cooling catheter is circulated at 5 cc/sec. The saline travels through the heat exchanger in the chilled water bath and is cooled to approximately 1° C.
14. The saline subsequently enters the cooling catheter where it is delivered to the heat transfer element. The saline is warmed to approximately 5–7° C. as it travels along the inner lumen of the catheter shaft to the end of the heat transfer element.
15. The saline then flows back through the heat transfer element in contact with the inner metallic surface. The saline is further warmed in the heat transfer element to 12–15° C., and in the process, heat is absorbed from the blood, cooling the blood to 30° C. to 35° C.
16. The chilled blood then goes on to chill the body. It is estimated that less than an hour will be required to substantially reduce a fever down to normothermia.
17. The warmed saline travels back the outer lumen of the catheter shaft and is returned to the chilled water bath where the same is cooled to 1° C.
18. The pressure drops along the length of the circuit are estimated to be between 1 and 10 atmospheres.
19. The cooling can be adjusted by increasing or decreasing the flow rate of the saline. Monitoring of the temperature drop of the saline along the heat transfer element will allow the flow to be adjusted to maintain the desired cooling effect.
20. The catheter is left in place to provide cooling for, e.g., 6–48 hours.

Of course, the use of the superior vena cava is only exemplary. It is envisioned that the following veins may be appropriate to percutaneously insert the heat transfer element: femoral, internal jugular, subclavian, and other veins of similar size and position. It is also envisioned that the following veins may be appropriate in which to dispose the heat transfer element during use: inferior vena cava, superior vena cava, femoral, internal jugular, and other veins of similar size and position. Arteries may also be employed if a fever therapy selective to a particular organ or region of the body is desired.

Figure 5:
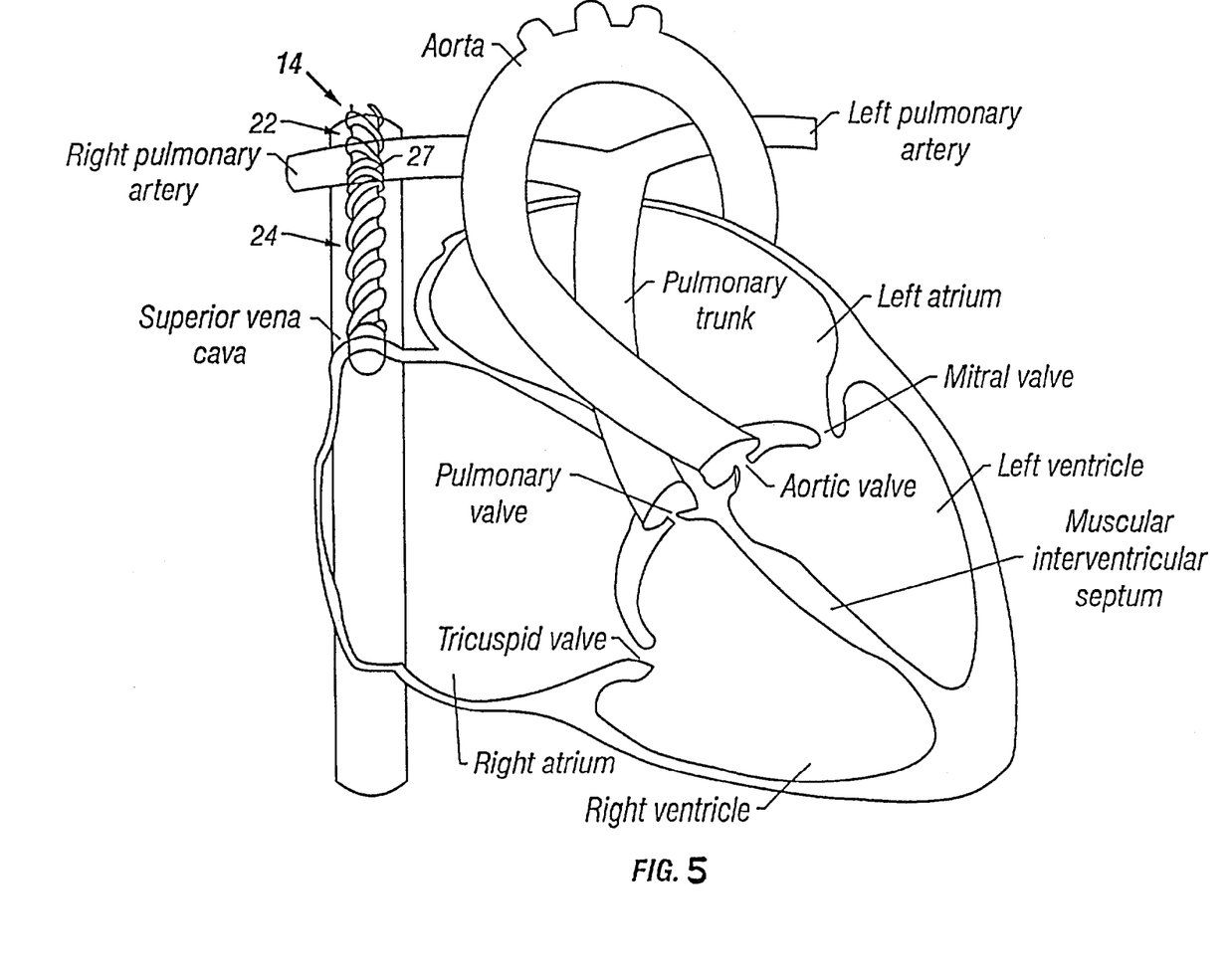
FIG. 5 is a schematic representation of the heat transfer element being used in an embodiment within the superior vena cava.

FIG. 5 shows a cross-section of the heart in which the heat transfer element 14 is disposed in the superior vena cava 62. The heat transfer element 14 has rotating helical grooves 22 as well as counter-rotating helical grooves 24. Between the rotating and the counter-rotating grooves are bellows 27. It is believed that a design of this nature would enhance the Nusselt number for the flow in the superior vena cava by about 5 to 80.

In some cases, a heating blanket may be used. The heating blanket serves several purposes. By warming the patient, vasoconstriction is avoided. The patient is also made more comfortable. For example, it is commonly agreed that for every one degree of core body temperature reduction, the patient will continue to feel comfortable if the same experiences a rise in surface area (skin) temperature of five degrees. Spasms due to total body hypothermia may be avoided. Temperature control of the patient may be more conveniently performed as the physician has another variable (the amount of heating) which may be adjusted.

As an alternative, the warming element may be any of the heating methods proposed in U.S. patent application Ser. No. 09/292,532, filed on Apr. 15, 1999, and entitled "Isolated Selective Organ Cooling Method and Apparatus," and incorporated by reference above.

Anti-shivering drugs may be used to provide the features of the heating blanket. In this connection, meperidine is an analgesic of the phenyl piperdine class that is known to bind to the opiate receptor. Meperidine may be used to treat shivering due to post-operative anesthesia as well as hypothermia induced in a fever suppression treatment.

In a method according to an embodiment of the invention for treating patients with fever, the heat transfer element as described may be placed in any of several veins, including the femoral, the IVC, the SVC, the subclavian, the braichiocephalic, the jugular, and other such veins. The heat transfer element may also be placed in appropriate arteries for more selective fever reduction.

The amount of cooling performed may be judged to a first approximation by the rate of cool-down. The amount of cooling is proportional to the difference between the temperature of the blood and the temperature of the heat transfer element or cooling element. Thus, if the temperature of the blood is 40° C. and the temperature of the cooling element is 5° C., the power extracted will be greater than if the temperature of the blood is 38° C. and the temperature of the cooling element is maintained at 5° C. Thus, the cool-down or cooling rate is generally greatest at the beginning of a cooling procedure. Once the patient temperature begins to approach the target temperature, usually normothermia or 37° C., the cooling rate may be reduced because the temperature differential is no longer as great.

In any case, once the patient reaches the normothermic temperature, it is no longer easy to guess whether, in the absence of the cooling therapy, the patient would otherwise be feverish or whether the fever has abated. One embodiment of the invention allows a determination of this.

First, it is noted that the power extracted can be calculated from the temperature differential between the working fluid supply temperature and the working fluid return temperature. In particular:

$$P_{catheter} = M \, c_f \Delta T_f$$

Where $P_{catheter}$ is the power extracted, M is the mass flow rate of the working fluid, $c_f$ is the heat capacity of the working fluid, and ΔT is the temperature differential between the working fluid as it enters the catheter and as it exits the catheter. Accordingly, $P_{catheter}$ can be readily calculated by measuring the mass flow of the circulating fluid and the temperature difference between the working fluid as it enters and exits the catheter. The power removed by the catheter as determined above may be equated to a close approximation to the power that is lost by the patient's body.

In general, a closed-form solution for the power P required to cool (or heat) a body at temperature T to temperature $T_0$ is not known. One possible approximation may be to assume an exponential relationship:

$$P = \alpha(\exp\beta(T-T_o)-1)$$

Taking the derivative of each side with respect to temperature:

$$\frac{\partial P}{\partial T} = \alpha\beta e^{\beta(T-T_0)}$$

and taking the inverse of each side:

$$\frac{\partial T}{\partial P} = \frac{1}{\alpha\beta e^{\beta(T-T_0)}}$$

or $$\Delta T \approx \frac{\partial T}{\partial P}\Delta P$$

where ΔT is the temperature differential from nominal temperature and ΔP is the measured power.

A close approximation may be obtained by assuming the relationship is linear. Equivalently, a power series expansion may be taken, and the linear term retained. In any case, integrating, assuming a linear relationship, and rearranging: $P=\alpha(T-T_0)$, where the constant of proportionality has units of watts/degree Celsius. One can determine the constant of proportionality a using two points during the therapy when both T and P are finite and known. One may be when therapy begins, i.e., when the patient has temperature T and the catheter is drawing power P. Another point may be obtained when $T=T_0$ and $P=P_0$.

Then, for any P, T is given by:

$$T_{absence\ of\ therapy} = T_0 + \frac{P_{at\ T_0}}{\alpha}$$

Figure 6:
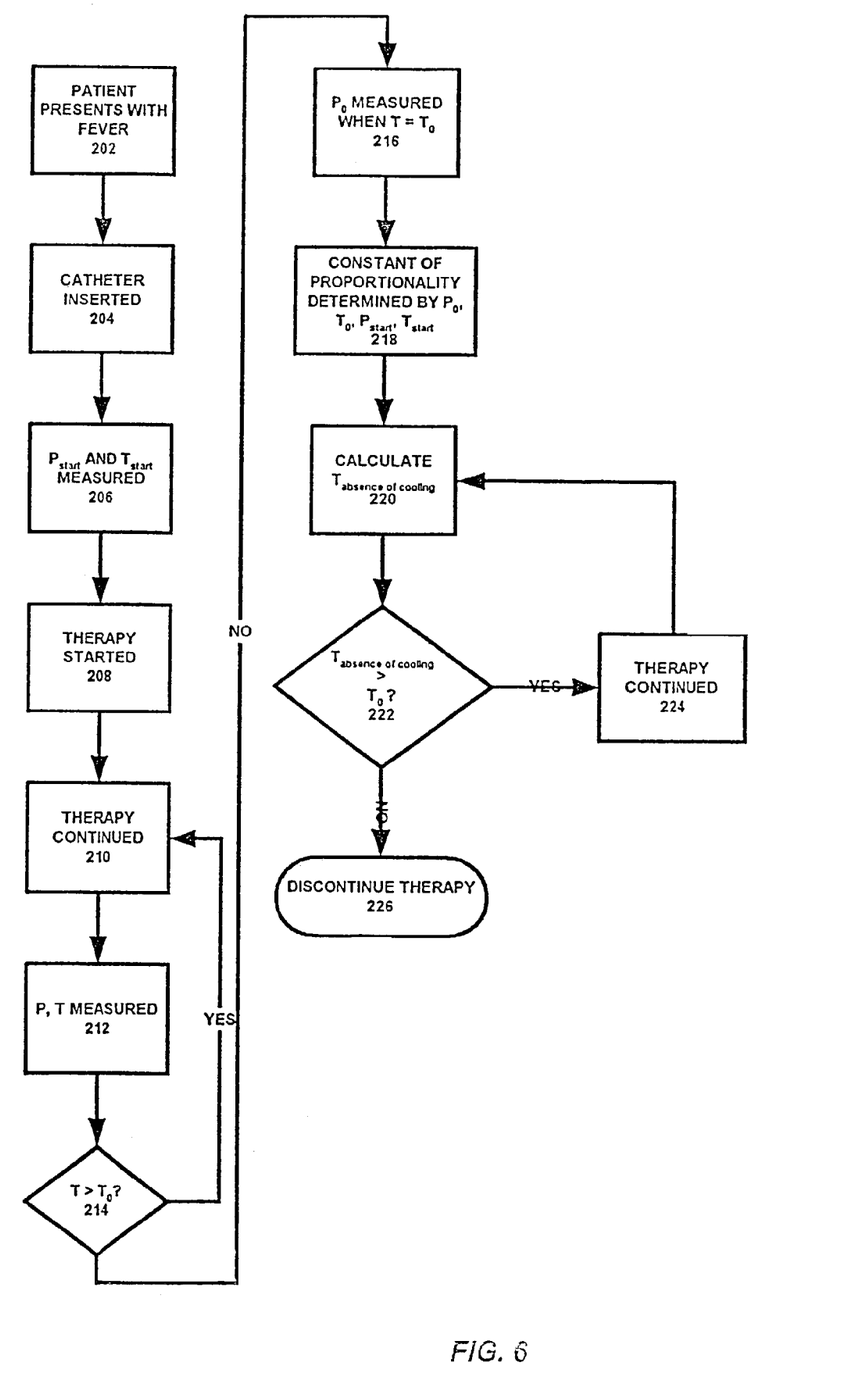
FIG. 6 is a flowchart showing an exemplary method of the invention.

An example of this may be seen in FIG. 6, which shows a flowchart of an embodiment of a method of the invention. Referring to the figure, a patient presents at a hospital or clinic with a fever (step 202). Generally, such a patient will have a fever as a result of a malady or other illness for which hospitalization is required. For example, the majority of patients in ICUs present with a fever.

A catheter with a heat transfer element thereon may be inserted (step 204). The initial power withdrawn $P_{start}$ and body temperature $T_{start}$ may be measured (step 206), and the therapy begun (step 208). The therapy continues (step 210), and P and T are periodically, continuously, or otherwise measured (step 212). The measured T is compared to the normothermic $T=T_0$, which is usually about 37° C. (step 214). If T is greater than T0, the therapy continues (step 210). If T is less than $T_0$, then the power $P_0$ is measured at $T=T_0$ (step 216). By the equations above, a constant of proportionality a may be uniquely determined (step 218) by knowledge of $T_{start}$, $P_{start}$, $P_0$, and $T_0$. From α, $T_{start}$, $P_{start}$, $P_0$, and $T_0$, $T_{absence\ of\ cooling}$ may be determined (step 220). $T_{absence\ of\ cooling}$ is then compared to $T_0$ (step 222). If $T_{absence\ of\ cooling} > T_0$, then the patient is still generating enough power via their metabolism to cause a fever if the therapy were discontinued. Thus, therapy is continued (step 224). If $T_{absence\ of\ cooling} <= T_0$, then the patient is no longer generating enough power via their metabolism to cause a fever if the therapy were discontinued. Thus, therapy is discontinued (step 226). Variations of the above method will be apparent to those of ordinary skill in the art.

While the invention herein disclosed is capable of obtaining the objects hereinbefore stated, it is to be understood that this disclosure is merely illustrative of the presently preferred embodiments of the invention and that no limitations are intended other than as described in the appended claims.

What is claimed is:

1. A method for treating fever in a patient's body intravascularly, comprising:
   providing a catheter having a flexible cooling element attached to a distal end thereof, wherein the catheter is flexible enough to navigate vasculature from the fernoral insertion point to an internal carotid artery;
   inserting the catheter through the vascular system of a patient with a fever to place the flexible cooling element in a vein that drains into the heart of a patient;
   circulating fluid through the cooling clement;
   transferring heat from the blood in the vein to the flexible cooling clement; and
   thereby lowering the temperature of the patient.

2. The method of claim 1, wherein the catheter includes flexible elements separated by inflexibie elements.

* * * * *